(12) United States Patent
Matheny

(10) Patent No.: US 9,308,084 B2
(45) Date of Patent: Apr. 12, 2016

(54) PROSTHETIC TISSUE VALVES AND METHODS FOR ANCHORING SAME TO CARDIOVASCULAR STRUCTURES

(71) Applicant: Robert G Matheny, Norcross, GA (US)

(72) Inventor: Robert G Matheny, Norcross, GA (US)

(73) Assignee: CORMATRIX CARDIOVASCULAR, INC, Roswell, GA (US)

( * ) Notice: Subject to any disclaimer, the term of this patent is extended or adjusted under 35 U.S.C. 154(b) by 39 days.

(21) Appl. No.: 14/229,854

(22) Filed: Mar. 29, 2014

(65) Prior Publication Data
US 2014/0330369 A1 Nov. 6, 2014

Related U.S. Application Data

(60) Provisional application No. 61/819,232, filed on May 3, 2013.

(51) Int. Cl.
*A61F 2/24* (2006.01)
(52) U.S. Cl.
CPC ............... *A61F 2/24* (2013.01); *A61F 2/2409* (2013.01); *A61F 2/2412* (2013.01); *A61F 2/2457* (2013.01)

(58) Field of Classification Search
CPC ....... A61F 2/24; A61F 2/2409; A61F 2/2454; A61F 2/2457
See application file for complete search history.

(56) References Cited

U.S. PATENT DOCUMENTS

| 8,734,841 B2* | 5/2014 | Matheny ............. A61L 27/3633 424/423 |
| 2005/0171616 A1* | 8/2005 | Sung et al. .................. 623/23.72 |
| 2006/0195183 A1* | 8/2006 | Navia et al. .................. 623/2.18 |
| 2009/0157177 A1 | 6/2009 | Matheny |
| 2010/0082094 A1 | 4/2010 | Quadri et al. |
| 2011/0066237 A1 | 3/2011 | Matheny |
| 2013/0310928 A1 | 11/2013 | Morriss et al. |
| 2014/0135911 A1 | 5/2014 | Spenser et al. |

* cited by examiner

*Primary Examiner* — David Isabella
*Assistant Examiner* — Suba Ganesan
(74) *Attorney, Agent, or Firm* — Francis Law Group

(57) ABSTRACT

A prosthetic atrioventricular tissue valve comprising a continuous tubular member formed from a first biocompatible material, the tubular member having proximal and distal ends, and at least one valve leaflet formed therein, the distal end of the tubular member including cardiovascular structure engagement means for connecting the tubular member to a cardiovascular structure, the cardiovascular structure engagement means comprising a plurality of elongated members that extend distally from the distal end of the tubular member.

11 Claims, 6 Drawing Sheets

PROSTHETIC TISSUE VALVES AND METHODS FOR ANCHORING SAME TO CARDIOVASCULAR STRUCTURES

CROSS-REFERENCE TO RELATED APPLICATIONS

This application claims priority to U.S. Provisional Application No. 61,819,232, filed on May 3, 2013.

FIELD OF THE INVENTION

The present invention generally relates to prosthetic valves for replacing defective cardiovascular valves. More particularly, the present invention relates to prosthetic atrioventricular valves and methods for anchoring same to cardiovascular structures and/or tissue.

BACKGROUND OF THE INVENTION

As is well known in the art, the human heart has four valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIG. 1C, there are also five papillary muscles in the heart 100; three in the right ventricle 116 and two in the left ventricle 106. The anterior, posterior and septal papillary muscles 113a, 113b, 113c of the right ventricle 116 each attach via chordae tendinae 117a, 117b, 117c to the tricuspid valve 112. The anterior and posterior papillary muscles 103a, 103b of the left ventricle 106 attach via chordae tendinae 119a, 119b to the mitral valve 102.

Since heart valves are passive structures that simply open and close in response to differential pressures, the issues that can develop with valves are typically classified into two categories: (i) stenosis, in which a valve does not open properly, and (ii) insufficiency (also called regurgitation), in which a valve does not close properly. Stenosis and insufficiency can occur concomitantly in the same valve or in different valves.

Both of the noted valve abnormalities can adversely affect organ function and result in heart failure. For example, insufficiency of the inlet (atrioventricular) tricuspid valve 112 to the right ventricle 116 of the heart 100 results in regurgitation of blood back into the right atrium 114, which, serving to receive blood flow returning in the veins from the entire body, then results in turn in suffusion and swelling (edema) of all the organs, most notably in the abdomen and extremities, insufficient forward conduction of blood flow from the right ventricle 116 into the lungs causing compromise of pulmonary function, and ultimately pump failure of the right heart. Collectively these conditions (collectively deemed right heart failure) can, and in many instances will, lead to incapacity and, possibly, death if progressive and uncorrected.

In addition to stenosis and insufficiency of a heart valve, surgical intervention may also be required for certain types of bacterial or fungal infections, wherein the valve may continue to function normally, but nevertheless harbors an overgrowth of bacteria (i.e. "vegetation") on the valve leaflets. The vegetation can, and in many instances will, flake off (i.e. "embolize") and lodge downstream in a vital artery.

If such vegetation is present on the valves of the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on the tricuspid valve can embolize to the lungs. The noted embolization can, and in many instances will, result in lung dysfunction.

Treatment of the noted heart valve dysfunctions typically comprises reparation of the diseased heart valve with preservation of the patient's own valve or replacement of the valve with a mechanical or bioprosthetic valve, i.e. a prosthetic valve.

Various prosthetic heart valves have thus been developed for replacement of natural diseased or defective heart valves. Illustrative are the tubular prosthetic tissue valves disclosed in Applicant's Co-Pending U.S. application Ser. Nos. 13/560, 573, 13/782,024, 13/782,289, 13/804,683, 13/182,170, 13/480,347 and 13/480,324. A further tubular prosthetic valve is disclosed in U.S. Pat. Nos. 8,257,434 and 7,998,196.

Heart valve replacement requires a great deal of skill and concentration to achieve a secure and reliable attachment of a prosthetic valve to a cardiovascular structure or tissue. Various surgical methods for implanting a prosthetic valve have thus been developed.

The most common surgical method that is employed to implant a prosthetic atrioventricular valve (mitral or tricuspid) comprises suturing a segment of one or more leaflets directly to the anterior and/or posterior papillary muscles.

A major problem associated with such attachment is that the papillary muscles and the region proximate thereto are subject to extreme stress (induced by cardiac cycles), which can, and in most instances will, adversely affect the structural integrity of the valve.

There is thus a need to provide improved prosthetic atrioventricular tissue valves and methods for attaching same to cardiovascular structures and/or tissue that maintain or enhance the structural integrity of the valve when subjected to cardiac cycle induced stress.

It is therefore an object of the present invention to provide improved prosthetic atrioventricular valves and methods for implanting same that overcome the drawbacks and disadvantages associated with conventional prosthetic atrioventricular valves.

It is another object of the present invention to provide improved prosthetic atrioventricular tissue valves and methods for attaching same to cardiovascular structures and/or tissue that maintain or enhance the structural integrity of the valve when subjected to cardiac cycle induced stress.

It is another object of the present invention to provide improved prosthetic atrioventricular tissue valves and methods for attaching same to cardiovascular structures and/or tissue that preserve the structural integrity of the cardiovascular structure(s) when attached thereto.

It is another object of the present invention to provide improved methods for securely attaching prosthetic atrioventricular valves to cardiovascular structures and/or tissue.

It is another object of the present invention to provide prosthetic atrioventricular tissue valves having means for secure, reliable, and consistently highly effective attachment to cardiovascular structures and/or tissue.

It is another object of the present invention to provide extracellular matrix (ECM) prosthetic atrioventricular tissue valves that induce host tissue proliferation, bioremodeling and regeneration of new tissue and tissue structures with site-specific structural and functional properties.

It is another object of the present invention to provide ECM prosthetic atrioventricular tissue valves that are capable of administering a pharmacological agent to host tissue and, thereby produce a desired biological and/or therapeutic effect.

SUMMARY OF THE INVENTION

The present invention is directed to prosthetic atrioventricular tissue valves that can be readily employed to selectively replace diseased or defective mitral and tricuspid valves, and methods for attaching (or anchoring) same to cardiovascular structures and/or tissue.

In a preferred embodiment of the invention, the prosthetic atrioventricular valves comprise continuous tubular members having proximal and distal ends.

In a preferred embodiment, the distal end of the tubular members includes cardiovascular structure engagement means that is designed and configured to securely engage the member and, hence, prosthetic atrioventricular tissue valve formed therefrom to cardiovascular structures, e.g., selective papillary muscles, ventricles, etc., and/or cardiovascular tissue.

In some embodiments, the cardiovascular structure engagement means comprises a plurality of valve leaflet extensions.

In some embodiments, the cardiovascular structure engagement means comprises a plurality of valve engagement regions formed by providing a recessed or scalloped distal end.

In some embodiments, the cardiovascular structure engagement means comprises a plurality of papillary muscle engagement tabs.

In some embodiments, the cardiovascular structure engagement means comprises a plurality of papillary muscle engagement ribbons.

In some embodiments of the invention, the cardiovascular structure engagement means comprises an integral region or component of the tubular members.

In some embodiments of the invention, the cardiovascular structure engagement means comprises a separate component or separate members.

In some embodiments of the invention, the cardiovascular structure engagement means and tubular members are formed from the same material.

In some embodiments of the invention, the cardiovascular structure engagement means and tubular members are formed from different materials.

In some embodiments of the invention, the tubular members (or a portion thereof) and/or cardiovascular structure engagement means comprise a biocompatible polymeric material.

In some embodiments of the invention, the tubular members (or a portion thereof) and/or cardiovascular structure engagement means comprise an extracellular matrix (ECM) material.

In a preferred embodiment of the invention, the ECM material comprises mammalian extracellular matrix tissue selected from the group comprising small intestine submucosa (SIS), urinary bladder submucosa (UBS), stomach submucosa (SS), central nervous system tissue, mesodermal tissue, i.e. mesothelial tissue, dermal extracellular matrix, subcutaneous extracellular matrix, gastrointestinal extracellular matrix, i.e. large and small intestines, tissue surrounding growing bone, placental extracellular matrix, ornomentum extracellular matrix, cardiac extracellular matrix, e.g., pericardium and/or myocardium, kidney extracellular matrix, pancreas extracellular matrix, lung extracellular matrix, and combinations thereof.

In some embodiments of the invention, the tubular members (or a portion thereof) and/or cardiovascular structure engagement means include at least one additional biologically active agent or composition, i.e. an agent that induces or modulates a physiological or biological process, or cellular activity, e.g., induces proliferation, and/or growth and/or regeneration of tissue.

In some embodiments of the invention, the biologically active agent comprises a growth factor.

In some embodiments of the invention, the biologically active agent comprises a cell.

In some embodiments, the tubular members (or a portion thereof) and/or cardiovascular structure engagement means include at least one pharmacological agent or composition (or drug), i.e. an agent or composition that is capable of producing a desired biological effect in vivo, e.g., stimulation or suppression of apoptosis, stimulation or suppression of an immune response, etc.

In some embodiments of the invention, the pharmacological agent comprises an anti-inflammatory agent.

In some embodiments of the invention, the pharmacological agent comprises a statin, i.e. a HMG-CoA reductase inhibitor.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
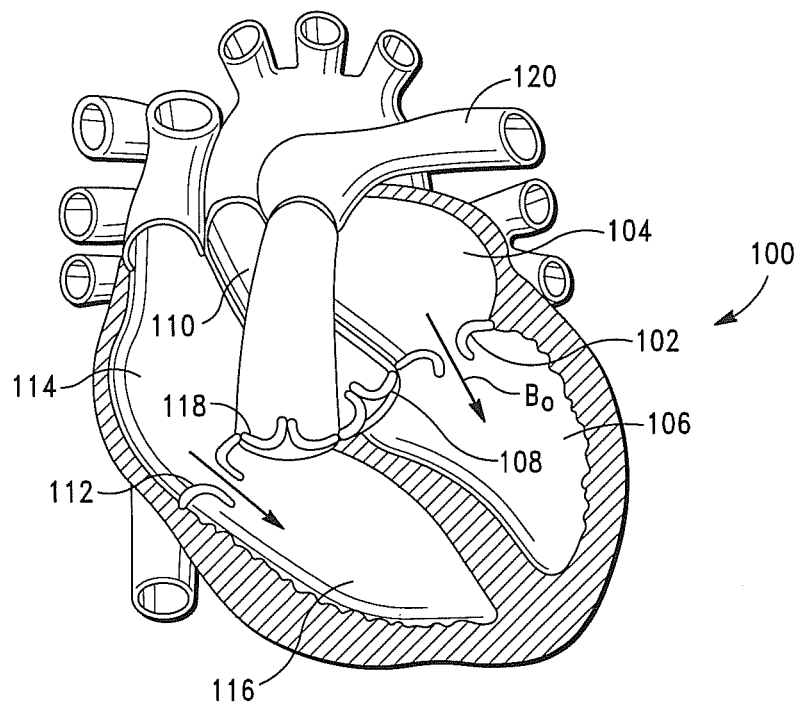
FIGS. 1A-1C are schematic illustrations of a human heart.
Figure 1B:
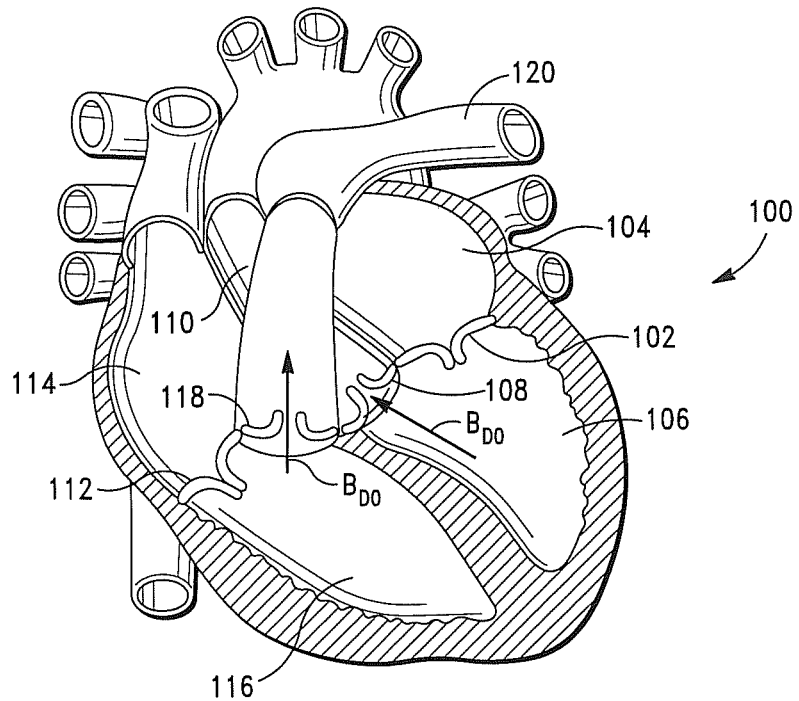
Figure 1C:
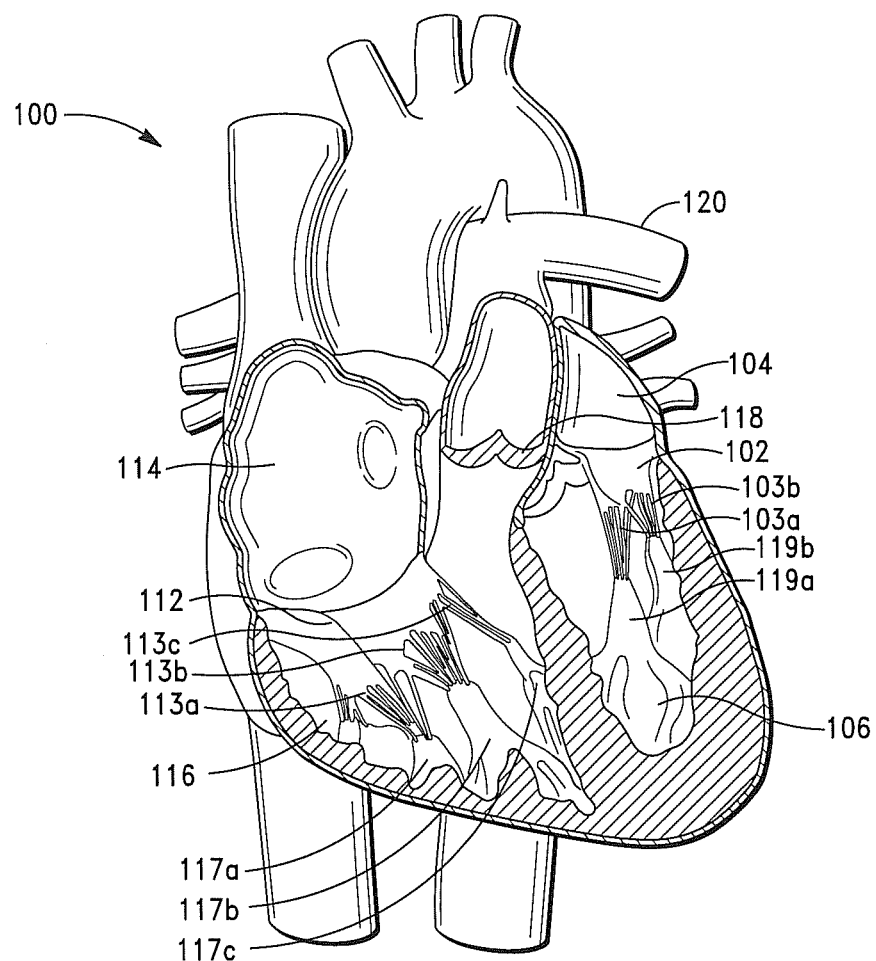

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

The terms "biologically active agent" and "biologically active composition" also mean and include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, ostepontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, antiviral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oxytetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "pharmacological agent", "active agent", "drug" and "active agent formulation" can further include one or more classes of cytotoxic anti-neoplastic agents or chemotherapy agents, including, without limitation, alkylating agents, cisplatin, carboplatin, oxaliplatin, mechlorethamine, cyclophosphamide, chlorambucil, and ifosfamide.

Chemotherapy agents can also include, without limitation, antimetabolites, such as purine analogues, pyrimidine analogues and antifolates, plant alkaloids, such as vincristine, vinblastine, vinorelbine, vindesine, podophyllotoxin, etoposide and teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibody treatments, such as abciximab, adalimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sennetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "pharmacological composition", as used herein, means and includes a composition comprising a "pharmacological agent" and/or a "biologically active agent" and/or any additional agent or component identified herein.

The term "therapeutically effective", as used herein, means that the amount of the "pharmacological agent" and/or "biologically active agent" and/or "pharmacological composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to prosthetic atrioventricular tissue valves that can be readily employed to selectively replace diseased or defective mitral and tricuspid valves, and methods for attaching same to cardiovascular structures and tissue.

As discussed in detail herein, the prosthetic atrioventricular (AV) valves comprise continuous tubular members defining a lumen and having first (or proximal) and second (or distal) ends, such as the tubular prosthetic valves disclosed in Co-Pending U.S. application Ser. Nos. 13/480,347 and 13/480,324; which are incorporated by reference herein.

In some embodiments of the invention, wherein the tubular members comprise an extracellular matrix (ECM) material, the tubular members remodel and regenerate (or form) at least one valve leaflet in the lumen, following attachment to a heart, i.e. annular region and papillary muscles, such as disclosed in U.S. application Ser. No. 13/480,347. In some embodiments, the tubular structure has a pre-deployment structure, e.g. inward folded region, that facilitates regeneration of at least one valve leaflet in the lumen, following attachment to a heart, such as disclosed in U.S. application Ser. No. 13/480,324.

In some embodiments, the tubular members include at least one pre-formed valve leaflet, such as disclosed in Co-Pending U.S. application Ser. Nos. 13/804,683 and 13/782,289, which are incorporated by reference herein in their entirety.

As discussed in detail herein, it is contemplated that, following implantation of a prosthetic ECM atrioventricular valve of the invention, the ECM atrioventricular valve can become populated with cells from the subject that will gradually remodel the ECM material of the valve into cardiovascular tissue that is identical or substantially identical to functioning cardiovascular tissue of a native atrioventricular valve, e.g., an defective atrioventricular valve that is being replaced with an ECM atrioventricular valve. It is further contemplated that, following remodeling, the tubular members of the prosthetic ECM atrioventricular valves will regenerate valve leaflets identical or substantially identical to functioning atrioventricular valve leaflets.

It is further contemplated that stem cells can migrate to the prosthetic ECM atrioventricular valves from the points at which the valve is attached to the papillary muscles and the annular region within the heart of a subject. It is still further contemplated that, during circulation of epithelial and endothelial progenitor cells, the surfaces of the prosthetic ECM atrioventricular valves can rapidly become lined or covered with epithelial and/or endothelial progenitor cells.

It is still further contemplated that the points at which a prosthetic ECM atrioventricular valve is attached to the papillary muscles and annular region can serve as points of constraint that direct the remodeling of the ECM atrioventricular valves into leaflet tissue and/or chordae tendineae that are identical or substantially identical to properly functioning native leaflet tissue and properly functioning native chordae tendineae.

It is still further contemplated that, where the annulus is removed from the annular region prior to attachment of a prosthetic ECM atrioventricular valve, the inlet portion of the ECM atrioventricular valve can direct the remodeling of an annulus that is identical or substantially identical to a properly functioning native annulus.

As indicated above, in a preferred embodiment of the invention, the second or "distal" end of the tubular members includes cardiovascular structure engagement means that is designed and configured to securely engage the member and, hence, prosthetic atrioventricular tissue valves to cardiovascular structures, e.g., selective papillary muscles, ventricles, etc., and/or cardiovascular tissue.

According to the invention, the tubular members and, hence, prosthetic atrioventricular valves formed therefrom, can comprise various biocompatible materials.

In some embodiments of the invention, the tubular members (or a portion thereof) and/or cardiovascular structure engagement means comprise a biocompatible polymeric material. In some embodiments, the polymeric material comprises Dacron, polyether ether ketone (PEEK), and like materials.

In some embodiments of the invention, the tubular members (or a portion thereof) and/or cardiovascular structure engagement means comprise an extracellular matrix (ECM) material.

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety.

In a preferred embodiment, the mammalian tissue sources include, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

As stated above, in some embodiments of the invention, the tubular members (or a portion thereof) and/or cardiovascular structure engagement means include at least one additional biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents, including, without limitation, the aforementioned cells and proteins.

In some embodiments, the tubular members (or a portion thereof) and/or cardiovascular structure engagement means include at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises an anti-inflammatory agent.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. The properties and beneficial actions are set forth in Applicant's Co-Pending application Ser. No. 13/373,569, filed on Sep. 24, 2012 and Ser. No. 13/782,024, filed on Mar. 1, 2013; which are incorporated by reference herein in their entirety.

In some embodiments of the invention, the pharmacological agent comprises chitosan. As also set forth in detail in Co-Pending application Ser. No. 13/573,569, chitosan also exhibits numerous beneficial properties that provide several beneficial biochemical actions or activities.

Figure 2:
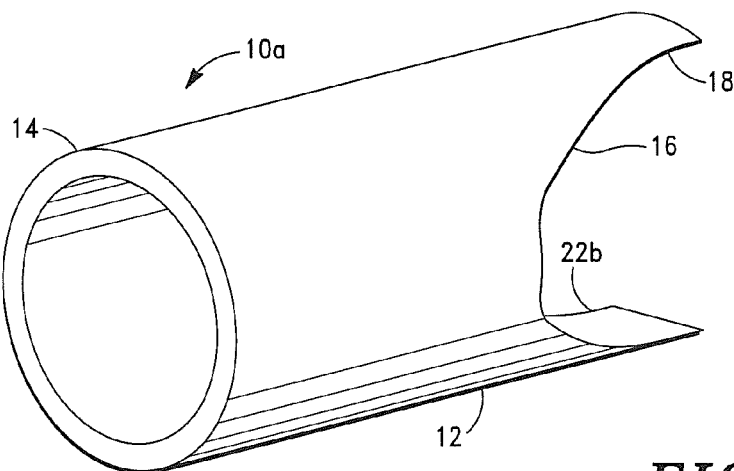
FIG. 2 is a perspective view of one embodiment of a prosthetic atrioventricular tissue valve, in accordance with the invention.
Figure 3:
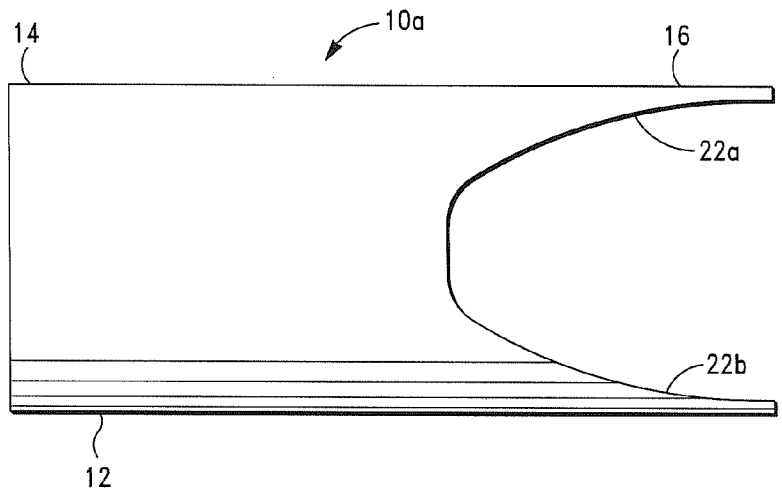
FIG. 3 is a side plane view of the prosthetic atrioventricular tissue valve shown in FIG. 2, in accordance with the invention.
Figure 4:
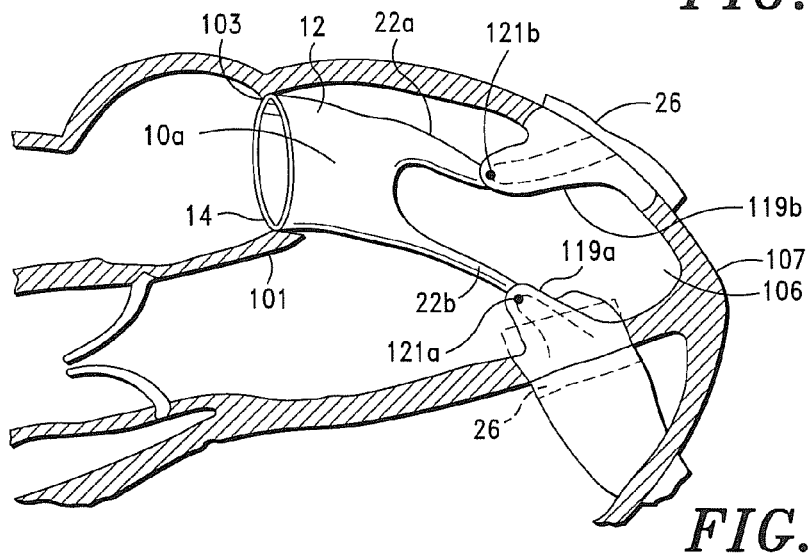
FIG. 4 is an illustration of the prosthetic atrioventricular tissue valve shown in FIG. 2 implanted in a cardiovascular vessel, in accordance with the invention.

Referring now to FIGS. 2-4, one embodiment of a prosthetic atrioventricular tissue valve will be described in detail.

As illustrated in FIGS. 2 and 3, the prosthetic atrioventricular tissue valve 10a comprises a continuous tubular member 12 having first or "proximal" and second or "distal" ends 14, 16. In some embodiments of the invention, the valve 10 includes at least one internal leaflet, such as disclosed in Co-Pending U.S. application Ser. Nos. 13/804,683 and 13/782,289. In some embodiments, the tubular member 12 includes a leaflet forming interior surface, such as disclosed in Co-Pending U.S. application Ser. Nos. 13/480,324 and 13/480,347.

According to the invention, the tubular member 12 can comprise various biocompatible materials, including, without limitation, mammalian tissue, e.g., bovine tissue.

In some embodiments of the invention, the tubular member 12 comprises a biocompatible polymeric material. In some embodiments, the polymeric material comprises Dacron, polyether ether ketone (PEEK), and like materials.

In a preferred embodiment, the tubular member 12 comprises an extracellular matrix (ECM) material.

According to the invention, the ECM material can be derived from various mammalian tissue sources including, without limitation, small intestine submucosa (SIS), urinary bladder submucosa (UBS), stomach submucosa (SS), central nervous system tissue, mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornomentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

In some embodiments of the invention, the tubular member 12 includes at least one additional biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents.

In some embodiments, the tubular member 12 includes at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In a preferred embodiment, the second or "distal" end 16 of the tubular member 12 includes cardiovascular structure engagement means 18 that is designed and configured to securely engage the member 12 and, hence, prosthetic atrioventricular tissue valve 10a formed therefrom to cardiovascular structures, such as selective papillary muscles, and/or cardiovascular tissue.

As illustrated in FIGS. 2 and 3, in some embodiments, the cardiovascular structure engagement means 18 comprises a pair of valve leaflet extensions 22a, 22b, which, in some embodiments, extend from a valve leaflet to mimic the chordae tendinae. According to the invention, the valve leaflet extensions 22a, 22b can be disposed at various positions about the periphery of the distal end 16 of the tubular member 12.

In some embodiments of the invention, wherein the prosthetic atrioventricular tissue valve 10a is employed to replace a mitral valve, the leaflet extensions 22a, 22b are spaced at approximately 0° and 120° about the periphery of the distal end 16 of the tubular member 12.

According to the invention, the valve leaflet extensions 22a, 22b can also have various predetermined lengths to accommodate attachment to desired cardiovascular structures, e.g., selective papillary muscles.

In some embodiments of the invention, the valve leaflet extensions 22a, 22b comprise an integral region or integral members. In some embodiments, the valve leaflet extensions 22a, 22b comprise separate members.

According to the invention, the valve leaflet extensions 22a, 22b can comprise the same material as the tubular member 12 or a different material, e.g. tubular member 12 comprises SIS and the valve leaflet extensions 22a, 22b comprise a polymeric material.

Referring now to FIG. 4, implantation of the prosthetic atrioventricular tissue valve 10a will be described in detail. According to the invention, the valve 10a is initially disposed proximate the target vessel region, e.g., mitral valve region. The initial placement or implantation of the valve 10a can be achieved by various conventional means, including limited access heart surgery and percutaneous delivery.

The proximal end 14 of the valve 12 is then sutured to the ventricle 100. In some embodiments, the valve leaflet extensions 22a, 22b are then attached directly to the papillary muscles 102a, 102b.

In some embodiments, the valve leaflet extensions 22a, 22b are threaded or implanted down through the papillary muscles 102a, 102b and attached to the outside 101 of the ventricle 100. In some embodiments, the valve leaflet extensions 22a, 22b are attached to a separate anchor 26 that is disposed on the outside 101 of the ventricle 100.

It is contemplated that, following attachment of the valve leaflet extensions 22a, 22b to the papillary muscles 102a, 102b, the valve leaflet extensions 22a, 22b fuse to the papillary muscles 102a, 102b and, in some instances, regenerate functioning native chordae tendineae.

As indicated above, it is also contemplated that the points at which the valve leaflet extensions 22a, 22b to the papillary muscles 102a, 102b and the proximal end 14 of the valve 12 is attached to the ventricle 100, i.e. annular region, can serve as points of constraint that direct the remodeling of the ECM atrioventricular valve 12 into leaflet tissue and/or chordae tendineae that are identical or substantially identical to properly functioning native valve tissue and properly functioning native chordae tendineae.

According to the invention, the valve leaflet extensions 22a, 22b and noted placement and attachment thereof significantly enhances the strength and, hence, structural integrity of the valve 10a. The valve leaflet extensions 22a, 22b and noted placement and attachment thereof also preserves the structural integrity of the papillary muscles 102a, 102b.

The valve leaflet extensions 22a, 22b (and noted placement and attachment thereof) thus significantly reduces the risk of suture failure and rupture of the prosthetic valve tissue proximate the papillary muscles 102a, 102b. The valve leaflet extensions 22a, 22b (and noted placement and attachment thereof) also significantly reduce the risk of rupture of the papillary muscles 102a, 102b.

Figure 5:
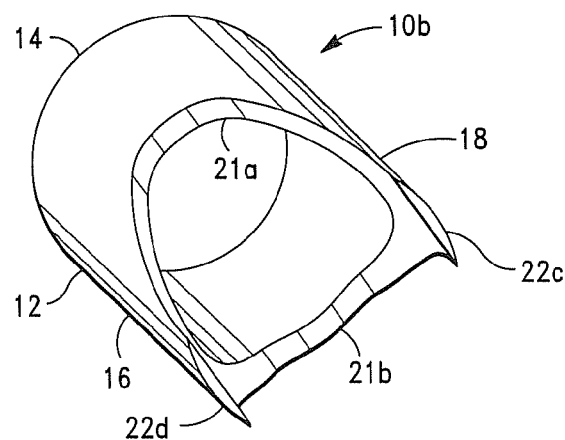
FIG. 5 is a perspective view of a further embodiment of prosthetic atrioventricular tissue valve having a scalloped distal end, in accordance with the invention.

Referring now to FIG. 5, there is shown another embodiment of a prosthetic atrioventricular tissue valve 10b of the invention. As illustrated in FIG. 5, the prosthetic valve 10b similarly comprises a continuous tubular member 12 having proximal and distal ends 14, 16. The distal end 16 of the tubular member 12 also includes cardiovascular structure engagement means 18 that is designed and configured to securely engage the member 12 and, hence, prosthetic atrioventricular tissue valve 10b formed therefrom to cardiovascular structures, e.g. selective papillary muscles, and/or cardiovascular tissue.

In this embodiment, the cardiovascular structure engagement means 18 is formed by providing a pair of opposing recessed or scalloped regions 21 proximate the distal end 16 of the tubular member 12, whereby two papillary muscle engagement members 22c, 22d are formed. The papillary muscle engagement members 22c, 22d are similarly designed and configured to attach to selective papillary muscles, e.g. papillary muscles 102a, 102b, and other cardiovascular structures, e.g., ventricles.

Thus, although the scalloped regions 21 are shown disposed at approximately 0° and 180°, the scalloped regions 21 and, hence, papillary muscle engagement members 22c, 22d formed thereby, can be spaced at different angles to accommodate attachment to selective papillary muscles and other cardiovascular structures.

According to the invention, the papillary muscle engagement members 22c, 22d are designed and configured to redistribute the stress exerted on the distal end 16 of the valve 10b during cardiac cycles, which similarly significantly reduces the risk of suture failure, rupture of the papillary muscles 102a, 102b, and prosthetic valve tissue proximate the papillary muscles 102a, 102b.

Figure 6:
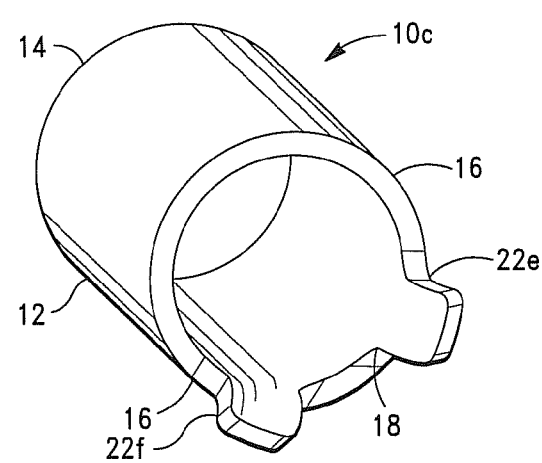
FIG. 6 is a perspective view of a further embodiment of prosthetic atrioventricular tissue valve having cardiovascular structure engagement tabs, in accordance with the invention.

Referring now to FIG. 6, there is shown another embodiment of a prosthetic atrioventricular tissue valve 10c of the invention. As illustrated in FIG. 6, the prosthetic valve 10c similarly comprises a continuous tubular member 12 having proximal and distal ends 14, 16. The distal end 16 of the tubular member 12 also includes cardiovascular structure engagement means 18 that is designed and configured to securely engage the member 12 and, hence, prosthetic atrioventricular tissue valve 10c to cardiovascular structures; particularly, papillary muscles, and/or tissue.

In this embodiment, the cardiovascular structure engagement means 18 comprises two papillary muscle engagement tabs 22e, 22f. According to the invention, the cardiovascular structure engagement means 18 can also comprise more than two tabs, e.g. 3, 4 tabs.

According to the invention, the papillary muscle engagement tabs 22e, 22f can similarly be disposed at various positions about the periphery of the distal end 16 of the tubular member 12 to accommodate attachment to desired cardiovascular structures; particularly, selective papillary muscles.

The papillary muscle engagement tabs 22e, 22f can similarly have various lengths and widths (and, hence, surface area) to accommodate attachment to desired cardiovascular structures, and to facilitate secure suture engagement.

According to the invention, the papillary muscle engagement tabs 22e, 22f are similarly designed and configured to redistribute the stress exerted on the distal end 16 of the valve 10c during cardiac cycles, significantly reducing the risk of suture failure and rupture of the papillary muscles 102a, 102b and prosthetic valve tissue proximate thereto.

Figure 7:
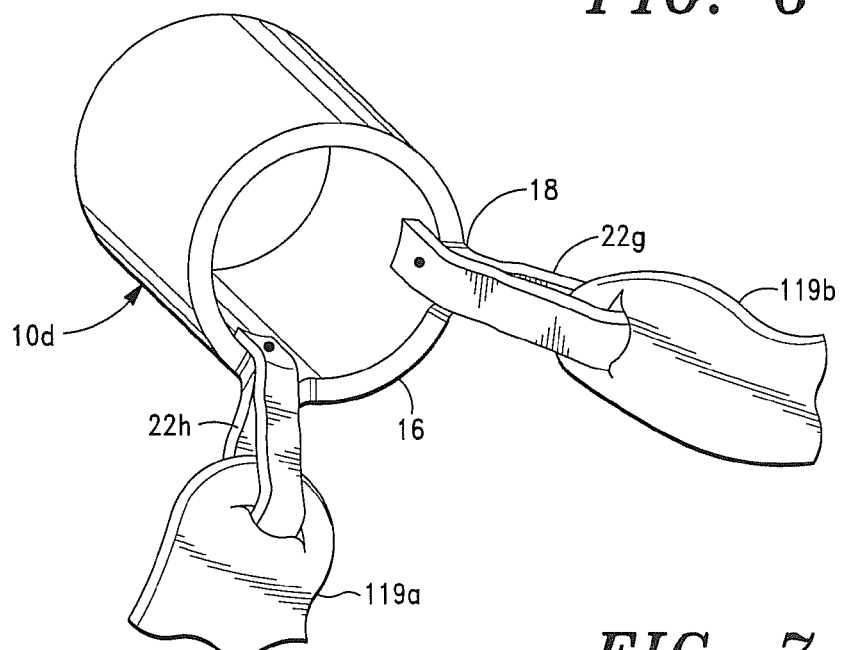
FIG. 7 is a perspective view of a further embodiment of prosthetic atrioventricular tissue valve having cardiovascular structure engagement ribbons, in accordance with the invention.

Referring now to FIG. 7, there is shown yet another embodiment of a prosthetic atrioventricular tissue valve 10d of the invention. As illustrated in FIG. 7, the prosthetic valve 10d similarly comprises a continuous tubular member 12 having proximal and distal ends 14, 16; the distal end 16 including cardiovascular structure engagement means 18 that is designed and configured to securely engage the valve 10d to cardiovascular structures; particularly, papillary muscles, and/or tissue.

In this embodiment, the cardiovascular structure engagement means 18 comprises two papillary muscle engagement ribbons 22g, 22h. According to the invention, the cardiovascular structure engagement means 18 can also comprise more than two ribbons, e.g. 3, 4 ribbons.

According to the invention, the papillary muscle engagement ribbons 22g, 22h can similarly be disposed at various positions about the periphery of the distal end 16 of the tubular member 12 to accommodate attachment to desired cardiovascular structures; particularly, selective papillary muscles.

The papillary muscle engagement ribbons 22g, 22h can also have various lengths and widths (and, hence, surface area) to accommodate desired cardiovascular structure and/or tissue attachment locations, and to facilitate secure suture engagement. According to the invention, each engagement ribbon 22g, 22h can have a tapered configuration, i.e. wider region proximate the base or valve distal end 16.

As illustrated in FIG. 7, in a preferred embodiment, each ribbon 22g, 22h has sufficient length to transition though a desired region of a respective papillary muscle 102a, 102b and be looped back and attached to the distal end 16 of the valve 10d.

According to the invention, the papillary muscle engagement ribbons 22g, 22h are similarly designed and configured to redistribute the stress exerted on the distal end 16 of the valve 10d during cardiac cycles, which significantly reduces the risk of suture failure and rupture of the papillary muscles 102a, 102b and prosthetic valve tissue proximate thereto.

According to the invention, it is similarly contemplated that, following attachment of the papillary muscle engagement tabs 22e, 22f and ribbons 22g, 22h to papillary muscles, the tabs 22e, 22f and ribbons 22g, 22h similarly fuse to the papillary muscles and, in some instances, regenerate functioning native chordae tendineae.

It is also contemplated that the points at which the papillary muscle engagement tabs 22e, 22f and ribbons 22g, 22h to papillary muscles can similarly serve as points of constraint that direct the remodeling of an ECM atrioventricular valve into chordae tendineae that are identical or substantially identical to properly functioning native chordae tendineae.

Figure 8:
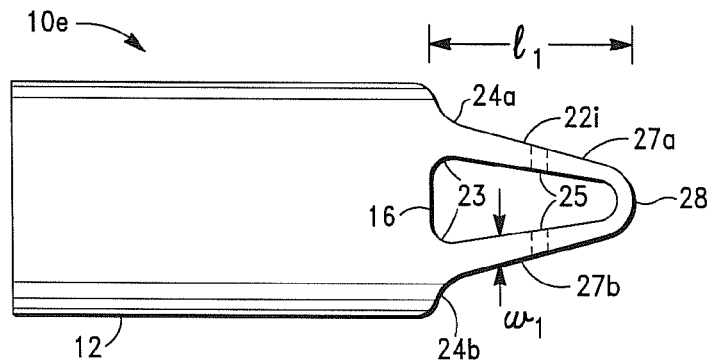
FIG. 8 is a side plan view of a further embodiment of prosthetic atrioventricular tissue valve having looped engagement members, in accordance with the invention.
Figure 9:
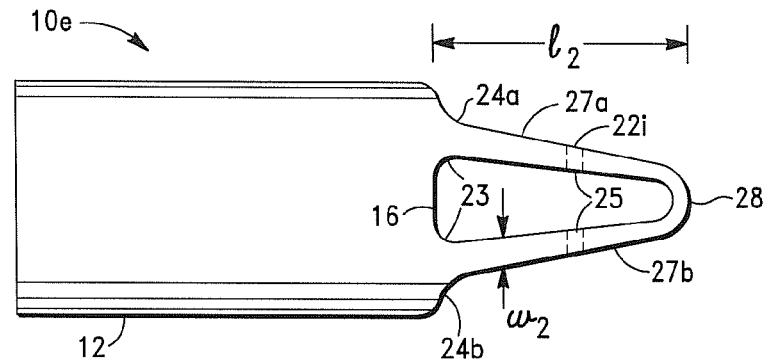
FIG. 9 is a side plan view of the prosthetic atrioventricular tissue valve shown in FIG. 8 in a stress position, in accordance with the invention.
Figure 10:
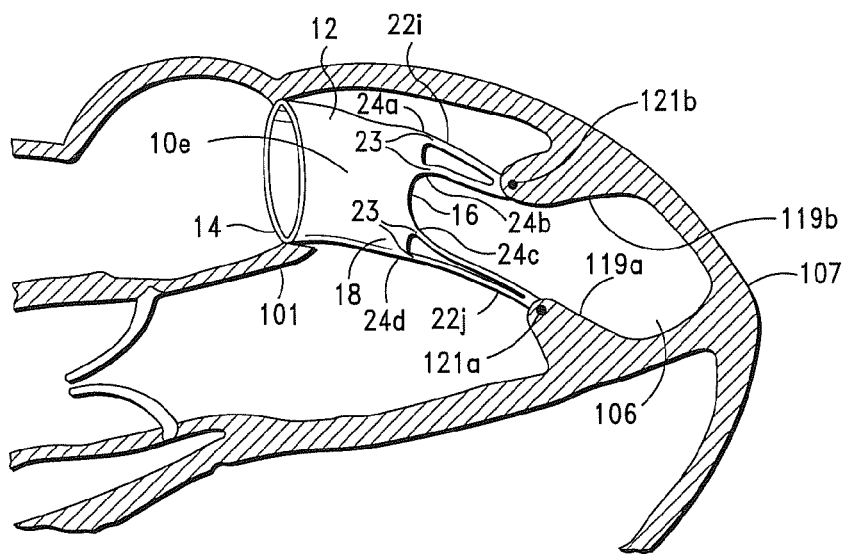
FIG. 10 is a schematic illustration of the prosthetic atrioventricular tissue valve shown in FIG. 8 attached to papillary muscles, in accordance with the invention.

Referring now to FIGS. 8-10, there is shown another embodiment of a prosthetic atrioventricular tissue valve 10e of the invention. As illustrated in FIG. 8, the prosthetic valve 10e similarly comprises a continuous tubular member 12 having proximal and distal ends 14, 16. The distal end 16 of the tubular member 12 also includes cardiovascular structure engagement means 18 that is designed and configured to securely engage the member 12 and, hence, prosthetic atrioventricular tissue valve 10e formed therefrom to cardiovascular structures, e.g. selective papillary muscles and/or cardiovascular tissue.

In this embodiment, the cardiovascular structure engagement means 18 comprises two looped engagement members 22i, 22j. As illustrated in FIG. 10, in a preferred embodiment, the looped engagement member 22i has first and second ends 24a, 24b, respectively, that are preferably integral with (or, in some embodiments, configured to attach to) the periphery of the distal end 16 of the tubular member 12. Looped engagement member 22j similarly has first and second ends 24c, 24d, respectively, that are preferably integral with the periphery of the distal end 16 of the tubular member 12.

In a preferred embodiment, the base of each engagement end 24a, 24b, 24c, 24d (denoted "23) has a larger width than the ends 28 of the engagement members 22i, 22j and, hence, radial end 28 of the looped engagement members 22i, 22j. Thus, as illustrated in FIGS. 8 and 9, in some embodiments, the opposing regions (or legs) 27a, 27b of the engagement members 22i, 22j have a substantially tapered shape.

In some embodiments of the invention, each engagement member 22i, 22j further includes at least one pleated region, more preferably, at least two pleated regions 25 that are disposed proximate the looped end 28 of each member 22i, 22j to enhance the structural integrity of each member 22i, 22j.

In a preferred embodiment, the first and second ends 24a, 24b of looped member 22i, and the first and second ends 24c, 24d of looped member 22j are preferably spaced apart about the periphery of the distal end 16 of the tubular member 12 in the range of approximately 5-10°, more preferably, in the range of approximately 5-30°.

According to the invention, the engagement members 22i, 22j can similarly be disposed at various positions about the periphery of the distal end 16 of the tubular member 12 to accommodate attachment to desired cardiovascular structures; particularly, selective papillary muscles.

In some embodiments of the invention, wherein the prosthetic atrioventricular tissue valve 10e is employed to replace a mitral valve, the engagement members 22i, 22j are spaced apart on the periphery of the distal end 16 of the tubular member 12 in the range of approximately at approximately 0° and 120°.

The engagement members 22i, 22j can similarly have various lengths and widths (and, hence, surface area) to accommodate attachment to desired cardiovascular structures, and to facilitate secure suture engagement.

According to the invention, it is similarly contemplated that, following attachment of the engagement members 22i, 22j to the papillary muscles 102a, 102b, the engagement members 22i, 22j similarly fuse to the papillary muscles 102a, 102b and, preferably, regenerate functioning native chordae tendineae.

It is also contemplated that the points at which the papillary muscle engagement members 22i, 22j attach to papillary muscles 102a, 102b can similarly serve as points of constraint that direct the remodeling of an ECM atrioventricular valve into chordae tendineae that are identical or substantially identical to properly functioning native chordae tendineae.

According to the invention, the engagement members 22i, 22j are similarly designed and configured to redistribute the stress exerted on the distal end 16 of the valve 10c during cardiac cycles, significantly reducing the risk of suture failure and rupture of the papillary muscles 102a, 102b and prosthetic valve tissue proximate thereto.

Applicant has, however, found that valve 10e provides optimal stress distribution by virtue of the engagement members' looped configuration, tapered opposing regions and spacing thereof. Referring now to FIGS. 8 and 9, there is shown a side plan view of looped engagement member 22i.

Since the side plan view of engagement member 22j would be similar to the illustrated side plan view of engagement member 22i, for purposes of the discussion, only engagement member 22i is illustrated. The following discussion is thus also applicable to engagement member 22j.

Referring first to FIG. 8, there is shown engagement member 22i in a pre-deployment configuration, wherein the looped member 22i has a first length $l_1$. When the engagement member is attached to a papillary muscle and subjected to cardiac cycle induced stress, the looped member 22i transitions for the pre-deployment shape illustrated in FIG. 8 to the stress position illustrated in FIG. 9, wherein the looped member 22i has a second (i.e. stretched) length $l_2$.

A significant feature of the looped member 22i (and, hence, looped member 22j) is that when the looped engagement member 22i is attached to a papillary muscle and subjected to cardiac cycle induced forces and, hence, stresses, the induced forces are applied substantially linearly along the opposing sides or legs 27a, 27b of the engagement member 22i and distributed and, hence, exerted radially proximate the distal end 16 of the tubular member 12, as discussed in further detail below.

Figure 11:
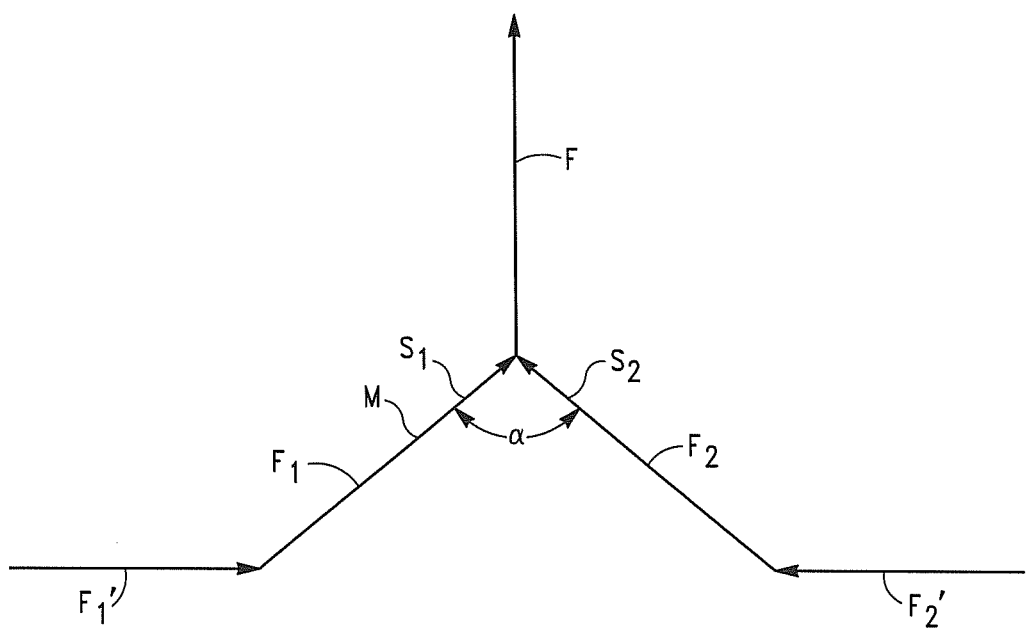
FIG. 11 is a schematic force diagram showing the force distribution exhibited by a looped engagement member, in accordance with the invention.

Referring now to FIG. 11, there is shown a schematic force diagram illustrating the force distribution provided by the looped engagement members of the invention, when subjected to a cardiac cycle induced force. As stated above, when a looped engagement member is subjected to a cardiac cycle induced force, denoted "F", the force F is transferred and applied to and, hence, shared by the opposing legs $S_1$, $S_2$ of the engagement member M, denoted "$F_1$" and "$F_2$". A portion of applied force F is also exerted radially proximate the ends of each opposing leg $S_1$, $S_2$, denoted radial forces "$F'_1$" and "$F'_2$", and, thus, exerted radially proximate the distal end 16 of a valve tubular member 12 associated therewith.

As is well known in the art, the sum of the forces "$F_1$", "$F'_1$", "$F_2$" and "$F'_2$" must equal the applied force "F", i.e. "$F_1$"+"$F'_1$"+"$F_2$"+"$F'_2$"=F.

As is also well known in the art, the forces exerted radially proximate each opposing leg $S_1$, $S_2$ and, hence, proximate the distal end 16 of a valve tubular member 12 associated therewith are directly related to, i.e. a function of, the angle formed proximate the juncture of the opposing legs $S_1$, $S_2$, denoted angle "$\alpha$".

In a preferred embodiment, angle "$\alpha$" is in the range of approximately 10°-35°, more preferably, in the range of approximately 15°-25°. Applicant has found that the noted angle "$\alpha$" values provide an optimal force distribution, i.e. forces "$F_1$", "$F'_1$", "$F_2$" and "$F'_2$" and, thereby, substantially enhanced structural integrity of the opposing legs $S_1$, $S_2$. The angle "$\alpha$" values and, hence, force distribution provided thereby also substantially enhance the structural integrity of a tubular member and, hence, valve associated with opposing legs $S_1$, $S_2$, whereby the probability of valve failure when subjected to cardiac cycle induced forces is substantially reduced.

It is also contemplated that the points at which the papillary muscle engagement members 22i, 22j transition to the distal end 16 of a valve tubular member 12 can serve as points of constraint that mediate cell-mediated contraction and ligand function.

As will readily be appreciated by one having ordinary skill in the art, the present invention provides numerous advantages compared to prior art prosthetic valves. Among the advantages are the following:

- The provision of improved methods for securely attaching prosthetic atrioventricular valves to cardiovascular structures and/or tissue.
- The provision of prosthetic atrioventricular tissue valves having means for secure, reliable, and consistently highly effective attachment to cardiovascular structures and/or tissue.
- The provision of improved prosthetic atrioventricular tissue valves and methods for attaching same to cardiovascular structures and/or tissue that maintain or enhance the structural integrity of the valve when subjected to cardiac cycle induced stress.
- The provision of improved prosthetic atrioventricular tissue valves and methods for attaching same to cardiovascular structures and/or tissue that preserve the structural integrity of the cardiovascular structure(s) when attached thereto.
- The provision of prosthetic atrioventricular tissue valves that induce host tissue proliferation, bioremodeling and regeneration of new tissue and tissue structures with site-specific structural and functional properties.
- The provision of prosthetic atrioventricular tissue valves that are capable of administering a pharmacological agent to host tissue and, thereby produce a desired biological and/or therapeutic effect.

The provision of prosthetic atrioventricular tissue valves that exhibit optimum mechanical compatibility with vascular structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic atrioventricular tissue valve, comprising:
a continuous tubular member comprising an extracellular matrix (ECM) composition, said ECM composition comprising acellular ECM from a mammalian tissue source, said tubular member further comprising proximal and distal ends, and at least one valve leaflet formed therein,
said proximal end of said tubular member being configured to attach to an annular valve region of a mammalian heart,
said distal end of said tubular member comprising integral cardiovascular structure engagement means for connecting said tubular member to papillary muscles, said cardiovascular structure engagement means comprising first and second elongated members that extend distally from said distal end of said tubular member,
said first elongated member comprising a first looped member having first and second ends and a first cardiovascular structure engagement region disposed between said first and second ends, said first cardiovascular structure engagement region being configured to engage a first papillary muscle, said first end of said first looped member being attached to a first transition region on said distal end of said tubular member and said second end of said first looped member being attached to a second transition region on said distal end of said tubular member,
said second elongated member comprising a second looped member having third and fourth ends and a second cardiovascular structure engagement region disposed between said third and fourth ends, said second cardiovascular structure engagement region being configured to engage a second papillary muscle, said third end of said second looped member being attached to a third transition region on said distal end of said tubular member and said fourth end of said second elongated member being attached to a fourth transition region on said distal end of said tubular member,
said tubular member being configured to regenerate new cardiovascular tissue and cardiovascular structures with site-specific structural and functional properties when said proximal end of said tubular member is engaged to an annular valve region of a mammalian subject's heart, said first elongated member is engaged to said first papillary muscle and said second elongated member is engaged to said second papillary muscle,
said tubular member being further configured to transition from a pre-implant configuration, wherein said first and second elongated members having a first length, to a post-implant configuration when said proximal end of said tubular member is engaged to said annular valve region at a valvular engagement region, said first elongated member first cardiovascular structure engagement region is engaged to said first papillary muscle at a first papillary muscle engagement region and said second elongated member second cardiovascular structure engagement region is engaged to said second papillary muscle at a second papillary muscle engagement region, wherein said first and second elongated members have a second length,
and wherein, when said proximal end of said tubular member is engaged to said annular valve region, said first elongated member first cardiovascular structure engagement region is engaged to said first papillary muscle and said second elongated member second cardiovascular structure engagement region is engaged to said second papillary muscle, and said tubular member is subjected to cardiac cycle induced forces, said first, second, third and fourth transition regions comprise first points of constraint, wherein said first, second, third and fourth transition regions mediate cell-mediated contraction and ligand function,
and wherein said first and second cardiovascular structure engagement regions comprise second points of constraint, wherein directed remodeling of said first and second elongated members and said first and second papillary muscle engagement regions is effectuated, wherein said first and second elongated members and said first and second papillary muscle engagement regions form properly functioning chordae tendineae,
and wherein said valvular engagement region comprises a third point of constraint, wherein directed remodeling of said annular heart region and said proximal end of said tubular member is effectuated, wherein said annular heart region and said proximal end of said tubular member form a functioning valve annulus.

2. The prosthetic atrioventricular tissue valve of claim 1, wherein said first and second attachment regions are spaced apart about the periphery of said distal end of said tubular member in the range of 5°-30° on said distal end of said tubular member, and wherein said third and fourth attachment regions are spaced in the range of 5°-30° on said distal end of said tubular member.

3. The prosthetic atrioventricular tissue valve of claim 1, wherein said first and second elongated members mimic chordae tendinae.

4. The prosthetic atrioventricular tissue valve of claim 1, wherein said mammalian tissue source is selected from the group comprising small intestine submucosa (SIS), urinary bladder submucosa (UBS), stomach submucosa (SS), mesothelial tissue, omentum extracellular matrix, cardiac extracellular matrix, kidney extracellular matrix, pancreas extracellular matrix, lung extracellular matrix, and combinations thereof.

5. A prosthetic atrioventricular tissue valve, comprising:
a continuous tubular member comprising an extracellular matrix (ECM) composition, said ECM composition comprising acellular ECM from a mammalian tissue source, said tubular member having proximal and distal ends, and at least one valve leaflet formed therein,
said proximal end of said tubular ECM member being configured to attach to an annular region of a heart of a subject,
said distal end of said tubular member comprising integral cardiovascular structure engagement means for connecting said distal end of said tubular member to papillary muscles disposed proximate said subject's heart, said cardiovascular structure engagement means comprising first and second elongated members that extend distally from said distal end of said tubular member,
said first elongated member comprising a first looped member having first and second ends and a first cardiovascular structure engagement region disposed between said first and second ends, said first cardiovascular structure engagement region being configured to engage a first papillary muscle, said first end of said first looped member being attached to a first transition region on said distal end of said tubular member and said second end of said first looped member being attached to a second transition region on said distal end of said tubular member, said second elongated member comprising a second looped member having third and fourth ends and a second cardiovascular structure engagement region disposed between said third and fourth ends, said second cardiovascular structure engagement region being configured to engage a second papillary muscle, said third end of said second looped member being attached to a third transition region on said distal end of said tubular member and said fourth end of said second elongated member being attached to a fourth transition region on said distal end of said tubular member, said first and second attachment regions being spaced apart about the periphery of said distal end of said tubular member in the range of 5°-30° on said distal end of said tubular member, and said third and fourth attachment regions being spaced in the range of 5°-30° on said distal end of said tubular member, said tubular member being configured to transition from a pre-implant configuration, wherein said first and second elongated members having a first length, to a post-implant configuration when said proximal end of said tubular member is engaged to said annular valve region at a valvular engagement region, said first elongated member first cardiovascular structure engagement region is engaged to said first papillary muscle at a first papillary muscle engagement region and said second elongated member second cardiovascular structure engagement region is engaged to said second papillary muscle at a second papillary muscle engagement region, wherein said first and second elongated members have a second length, and wherein said tubular member regenerates new cardiovascular tissue and said first and second elongated members fuse with said first and second papillary muscles, and wherein, when said proximal end of said tubular member is engaged to said annular valve region, said first elongated member first cardiovascular structure engagement region is engaged to said first papillary muscle and said second elongated member second cardiovascular structure engagement region is engaged to said second papillary muscle, and said tubular member is subjected to cardiac cycle induced forces, said first, second, third and fourth transition regions comprise first points of constraint, wherein said first, second, third and fourth transition regions mediate cell-mediated contraction and ligand function, and wherein said first and second cardiovascular structure engagement regions comprise second points of constraint, wherein directed remodeling of said first and second elongated members and said first and second papillary muscle engagement regions is effectuated, wherein said first and second elongated members and said first and second papillary muscle engagement regions form properly functioning chordae tendineae, and wherein said valvular engagement region comprises a third point of constraint, wherein directed remodeling of said annular heart region and said proximal end of said tubular member is effectuated, wherein said annular heart region and said proximal end of said tubular member form a functioning valve annulus.

6. The prosthetic atrioventricular tissue valve of claim 5, wherein said mammalian tissue source is selected from the group comprising small intestine submucosa (SIS), urinary bladder submucosa (UBS), stomach submucosa (SS), mesothelial tissue, omentum extracellular matrix, cardiac extracellular matrix, kidney extracellular matrix, pancreas extracellular matrix, lung extracellular matrix, and combinations thereof.

7. The prosthetic atrioventricular tissue valve of claim 6, wherein said ECM composition further includes a biologically active agent.

8. The prosthetic atrioventricular tissue valve of claim 7, wherein said biologically active agent comprises a growth factor selected from the group consisting of transforming growth factor alpha (TGF-alpha), transforming growth factor beta (TGF-beta), basic fibroblast growth factor (bFGF), and vascular epithelial growth factor (VEGF).

9. The prosthetic atrioventricular tissue valve of claim 7, wherein said biologically active agent comprises a cell selected from the group consisting of human embryonic stem cells, fetal cardiomyocytes, myofibroblasts, and mesenchymal stem cells.

10. The prosthetic atrioventricular tissue valve of claim 5, wherein said ECM composition further comprises a pharmacological agent selected from the group consisting of quinidine, procainamide, disopyramide, lidocaine, phenytoin, mexiletine, flecainide, propafenone, moricizine, propranolol, esmolol, timolol, metoprolol, atenolol, amiodarone, sotalol, ibutilide, dofetilide, amiodarone, sotalol, ibutilide, dofetilide, verapamil, diltiazem, adenosine and digoxin.

11. The prosthetic atrioventricular tissue valve of claim 5, wherein said ECM composition further comprises a HMG-CoA reductase inhibitor selected from the group consisting of atorvastatin, cerivastatin, fluvastatin, lovastatin, mevastatin, pitavastatin, pravastatin, rosuvastatin, and simvastatin.

* * * * *